(12) United States Patent
Peeters et al.

(10) Patent No.: US 11,266,378 B1
(45) Date of Patent: Mar. 8, 2022

(54) ENERGY COUPLING MATERIAL FOR WEARABLE ULTRASOUND DEVICES

(71) Applicant: Verily Life Sciences LLC, Mountain View, CA (US)

(72) Inventors: Eric Peeters, San Jose, CA (US); Benjamin David Krasnow, Redwood City, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 862 days.

(21) Appl. No.: 14/833,623

(22) Filed: Aug. 24, 2015

(51) Int. Cl.
*A61B 8/00* (2006.01)
*A61B 8/02* (2006.01)
*A61B 8/04* (2006.01)
*A61B 8/06* (2006.01)
*A61B 8/08* (2006.01)

(52) U.S. Cl.
CPC .............. *A61B 8/4281* (2013.01); *A61B 8/02* (2013.01); *A61B 8/04* (2013.01); *A61B 8/06* (2013.01); *A61B 8/4427* (2013.01); *A61B 8/4483* (2013.01); *A61B 8/488* (2013.01)

(58) Field of Classification Search
CPC .............................. A61B 8/4281; A61B 8/4272
See application file for complete search history.

(56) References Cited

U.S. PATENT DOCUMENTS

| | | | |
|---|---|---|---|
| 9,039,617 B2 | 5/2015 | Slayton et al. | |
| 2002/0082529 A1 | 6/2002 | Suorsa et al. | |
| 2003/0195420 A1 | 10/2003 | Mendlein et al. | |
| 2004/0138568 A1* | 7/2004 | Lo | A61B 8/4281 600/459 |
| 2005/0215901 A1* | 9/2005 | Anderson | A61B 8/12 600/445 |
| 2005/0240102 A1* | 10/2005 | Rachlin | A61B 8/10 600/437 |
| 2010/0068260 A1 | 3/2010 | Kruse et al. | |
| 2014/0276055 A1 | 9/2014 | Barthe et al. | |
| 2015/0135840 A1* | 5/2015 | Sato | A61N 7/00 73/644 |

* cited by examiner

*Primary Examiner* — Patricia J Park
(74) *Attorney, Agent, or Firm* — McDonnell Boehnen Hulbert & Berghoff LLP (57) ABSTRACT

An ultrasound device, including (i) an ultrasound transducer, and (ii) a coupling material in contact with the ultrasound transducer is presented. The coupling material can comprise a solid component and a liquid component, wherein the liquid component is absorbed within the solid component and forms a microscopic liquid layer on a surface of the solid component, through which acoustic energy from the ultrasound transducer can be conducted. The device can be mounted to an external body surface proximate to a portion of the lumen, allowing the device to measure the rate at which a component moves through the lumen. Also provided are methods for making the device and using the device to determine a physiological parameter based on at least the flow rate of a component through the lumen.

27 Claims, 7 Drawing Sheets

ENERGY COUPLING MATERIAL FOR WEARABLE ULTRASOUND DEVICES

BACKGROUND

Unless otherwise indicated herein, the materials described in this section are not prior art to the claims in this application and are not admitted to be prior art by inclusion in this section.

Ultrasound transducers, particularly Doppler ultrasound transducers, are a promising avenue for measuring several clinically relevant parameters for diagnostic and prognostic purposes. For example, heart rate, blood flow rate and blood pressure can be measured using Doppler ultrasound transducers. Ultrasound diagnostic devices use an energy coupling medium between the transducer and the skin. The energy coupling medium is typically a water-based liquid gel that is applied to the skin and/or ultrasound transducer. However, the use of wet coupling gels is not practical in a long-term device, especially in the case of a wearable consumer device. Dry coupling media are prone to drying out and are therefore also not favorable.

SUMMARY

Some embodiments of the present disclosure provide an ultrasound device, including: (i) an ultrasound transducer, and (ii) a coupling material in contact with the ultrasound transducer, where the coupling material comprises a solid component and a liquid component, where the liquid component is absorbed within the solid component and forms a microscopic liquid layer on a surface of the solid component, where at least a portion of the microscopic liquid layer is able to contact a target surface such that the coupling material is capable of conducting acoustic energy from the ultrasound transducer to the target surface via the microscopic liquid layer.

In some embodiments, the liquid component of the coupling material can be non-aqueous, such as an oil. The oil can be hydrocarbon, silicone or fluorosilicone based, or a mixture therefore. Similarly, the solid component of the coupling material can be non-aqueous, such as a polymer. The polymer can also be hydrocarbon, silicone, or fluorosilicone based, or a mixture therefore.

In other embodiments, the liquid component of the coupling material can be aqueous. In such embodiments, the solid component can include a polymer network, such as a cross-linked polymer, and a super-hygroscopic agent, such as polyacrylate or silica.

In some embodiments, the ultrasound device is wearable. For example, the ultrasound device may be included in a wristband or cuff.

In another aspect the disclosure also provides a method for making an ultrasound device. The method may include (i) combining a solid component and a liquid component to form a coupling material mixture, (ii) heating the coupling material mixture, (iii) placing the hot coupling material mixture on an ultrasound transducer, and (iv) cooling the coupling material mixture to form a coupling material on the ultrasound transducer, where the coupling material comprises a solid component and a liquid component, where the liquid component is absorbed within the solid component and forms a microscopic liquid layer on a surface of the solid component. The solid component and a liquid component can be as described above. For example, the solid component can be a polymer, and the liquid component can be an oil.

In another aspect the disclosure also provides a method for using an ultrasound device. The method may include:
(i) contacting a target surface with an ultrasound device, where the ultrasound device comprises:
   an ultrasound transducer; and
   a coupling material in contact with the ultrasound transducer, where the coupling material comprises a solid component and a liquid component, where the liquid component is absorbed within the solid component and forms a microscopic liquid layer on a surface of the solid component, and where at least a portion of the microscopic liquid layer contacts the target surface; and
(ii) transmitting an acoustic signal from the ultrasound transducer to the target surface via the microscopic liquid layer in contact with the target surface.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

An ultrasound device, such as a Doppler ultrasound device, can detect and measure one or more physiological parameters of a person in acoustic contact with the device (e.g., a person wearing the device). The one or more physiological parameters could include any parameters that relate to the person's health state. For example, the ultrasound signal detected by the device may be used to measure blood flow rate, heart rate, blood pressure, or other hemodynamic parameters.

The ultrasound device may include an ultrasound transducer and a coupling material. The coupling material is in contact with the ultrasound transducer and a target surface, and is capable of conducting acoustic energy from the ultrasound transducer to the target surface. The coupling material can include a solid component and a liquid component. The liquid component is absorbed within the solid component and forms a microscopic liquid layer on a surface of the solid component. The microscopic liquid layer allows the acoustic energy from the ultrasound transducer to reach the target surface with minimal acoustic impedance mismatches.

The coupling material of the ultrasound device can include a solid component and a liquid component. The solid component can be non-water soluble, such as a hydrocarbon-based polymer, or can be water soluble, such as an acrylate. Similarly, the liquid component can be aqueous, such as water, or non-aqueous, such as a hydrocarbon oil.

The ultrasound device may be a wearable device, which can include a mount that is configured to mount the device to a specific surface of the person's body, more particularly, to a body location where a physiological parameter is readily observable. For example, the wearable device can include a wristband for mounting the wearable device on the wrist. In this position, the wearable device may be only a few millimeters away from the subsurface vasculature, such as an artery, capillary or vein in the wrist. Other mounting locations include, but are not limited to, the forearm, upper arm, a finger or thumb, ankle, calf, torso or thigh.

In an example embodiment, the wearable device obtains at least some of the health-related information by detecting the movement of a component through the open space inside the subsurface vasculature (i.e., the lumen) to determine the flow rate of the component. In some embodiments, the component can be naturally present, such as a component of the blood (e.g., a circulating red blood cell). In other embodiments, the component can be introduced into a lumen by injection, ingestion, inhalation, transdermally, or in some other manner. Examples of introduced components include tracers, dyes, or any other component detectable by ultrasound.

The ultrasound device may be configured to activate on demand, such as at the push of a button, periodically, such as at certain times of every day (e.g., every hour), or continuously (e.g., every second or less).

The ultrasound device can also include one or more data collection systems that do not make use of ultrasound. For example, the ultrasound device can include sensors for measuring blood pressure, skin temperature, blood analyte, or other parameters. If in the form of a wristband, the wearable device may also include a watch face for displaying the time and/or date.

In addition, the ultrasound device may be configured to analyze the data that it collects. For example, the wearable device may include a computing device that is configured to detect the movement of a component through the lumen and, in some examples, to further determine the rate at which the component moves through the lumen. In some examples, a physiological parameter may be determined based, at least in part, on the fact that the rate at which the component moves through the lumen, such as when an indication of the medical condition is based on, at least, blood pressure or heart rate.

Other applications include the monitoring of one or more physiological parameters based on at least the flow rate of a component through a lumen. For example, blood pressure and/or heart rate may be monitored for a physical activity, such as athletic training or competition. The ultrasound device may also include a user interface that can display the results of the data analysis, such as the present heart rate of the wearer. The ultrasound device may also be configured to produce an auditory or tactile (vibration) response to alert the person wearing the device of a parameter (e.g., heart rate) that is higher or lower than desired. In this way, the person wearing the device can be made aware of a parameter, or related medical condition, in real time.

The ultrasound device may further include a communication interface for transmitting the results of the data analysis to medical personnel and/or receiving instructions or recommendations based on a medical personnel or remote computing device's interpretation of those results. In some examples, the communication interface is a wireless communication interface. The communication interface may also include a universal serial bus (USB) interface, a secure digital (SD) card interface, a wired interface, or any other appropriate interface for communicating data from the device to a server. The term "server" may include any system or device that responds to requests across a computer network to provide, or helps to provide, a network service, and may include servers run on dedicated computers, mobile devices, and those operated in a cloud computing network.

The ultrasound device may also be used in a method for monitoring cardiovascular health. A person may monitor physiological parameters by wearing the device on his or her person that is configured to on demand (e.g., at the push of a button), periodically (e.g., every minute) or continuously (e.g., every second or less) determine the wearer's blood pressure. If the device determines that the blood pressure is outside of a recommendation range (e.g., at an elevated level), the device may generate an alert through the user interface (e.g., an audible or tactile alarm). In some examples, the device may be configured to alert a third party through the communication interface, such as a family member or medical personnel.

Medical conditions may involve, at least as one indication of the condition, a low, high, or irregular heart rate. Tachycardia (high heart rate) can cause dizziness, lightheadedness, palpitations (rapid heartbeat), angina (chest pain), shortness of breath, unconsciousness, and even cardiac arrest. Similar symptoms and complications exist for bradycardia (low heart rate).

Medical conditions may also involve, at least as one indication of the condition, low, high, or irregular blood pressure. Hypertension (high blood pressure) can lead to problems such as coronary heart disease, heart failure, stroke, or kidney failure. Hypotension, (low blood pressure) can cause, dizziness, fainting, dehydration, nausea, blurred vision and fatigue. Thus, variations in blood pressure are important indicators of the risk of heart attack and/or stroke.

In an example, a person with tachycardia could use the ultrasound device to warn of an upcoming tachycardia episode before the aforementioned symptoms arise. In other embodiments, a person participating in athletic training or competition could use the ultrasound device to monitor heart performance, such as the time required to return to resting heart rate after physical activity. In another example, a person at risk for stroke or heart attack could use the ultrasound device to warn of an increased chance of stroke based on irregular blood pressure.

The wearable device may obtain data in each of a plurality of measurement periods. The length of the measurement period may be set on the device itself or may be set remotely, for example, by instruction from a remote server. The device may be configured with many measurement periods each day—for example, manual, continuous, every second, every minute, every hour, every 6 hours, etc. —or may be configured to take measurements once a week or once a month. The measurement periods can extend through a plurality of consecutive days (such as 30 or more days), and each of the consecutive days can include multiple measurement periods. In one example, the wearable device could measure the physiological parameters every hour, so that each of the consecutive days includes twenty-four measurement periods. In other examples, the ultrasound device could measure the physiological parameters more frequently or less frequently, or the ultrasound device could measure some of the physiological parameters more frequently than others.

Data representative of the physiological parameters may be used to develop an individual baseline profile for the wearer of the ultrasound device. The baseline profile may include patterns for how one or more of the wearer's physiological parameters typically change over time, such as during the course of a day, a week, or a month. The baseline profile may be developed on the ultrasound device itself (such as by a processor), or it may be developed by a remote server.

The ultrasound device may be configured to transmit certain data, such as the data representative of the physiological parameters, the baseline profile, etc., to a server, for example, via a wireless communication interface in the ultrasound device. In this way, the server may receive from the ultrasound device data regarding the plurality of physiological parameters for each of the plurality of measurement periods. The ultrasound device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

After a baseline profile for a wearer of the ultrasound device has been developed, either by the device or the server, additional data regarding the physiological parameters may be collected over additional measurement periods by the ultrasound device and may be compared to the baseline profile. Such comparison may be carried out on the ultrasound device itself, or by a remote server upon transmission of the additional data to the server. If the additional data is consistent with the patterns embodied in the baseline profile, the server may determine that the wearer's physiological parameters have not changed. On the other hand, if the additional data deviates from the patterns embodied in the baseline profile, the server may determine that the wearer's physiological parameters have changed. The change in physiological parameters may, for example, indicate that the wearer has developed a disease, disorder, or other adverse medical condition or may be at risk for a severe medical condition, such as a stroke or a heart attack, in the near future.

When a change in condition is detected, a clinical protocol may be consulted to generate one or more recommendations that are appropriate for the wearer's change in condition. For example, a recommendation that the wearer take a particular medication or supplement, schedule an appointment with a medical professional, go to the hospital to seek immediate medical attention, abstain from certain activities, etc. may be generated. The clinical protocol may be developed based, at least in part, on correlations between heart rate and health state of the wearer of the device, any known health information or medical history of the wearer, and/or on recognized standards of care in the medical field. Such actions may be carried out by a processor on the ultrasound device, or by a remote server.

Further, the ultrasound device may be configured to accept inputs from the wearer regarding his or her health state. The inputs may be subjective indicia regarding how the person is feeling or any symptoms he or she is experiencing at that time, such as, "feeling cold," "feeling tired," "stressed," "feeling rested and energetic," "pollen allergy symptoms today," etc. Such inputs from the user may be used to complement the physiological parameter data and establish correlations between the physiological parameter and health state.

The ultrasound device may be configured to accept, or the server may be configured to receive from some other source, certain environmental information. For example, information regarding the general health state of the population, such as when influenza or other viral outbreak has occurred, may be input into the system. Further, other general information that may affect the health of the population, such as daily pollen counts, pollution levels or the weather conditions may be input into the system. Such information may further be used to complement the physiological parameter data collected from individual wearers and populations of wearers of the device and establish correlations between the physiological parameter, health state and environmental factors.

Once generated, either by the server or the ultrasound device itself, the ultrasound device may provide an indication of the one or more recommendations via a user interface on the ultrasound device. The indication could be any indication that can be noticed by the person wearing the ultrasound device. For example, the indication could include a visual component (e.g., textual or graphical information on a display), an auditory component (e.g., an alarm sound), and/or tactile component (e.g., a vibration).

The ultrasound device and/or the server may also be configured to receive information regarding the actual health state of the wearer of the ultrasound device. This information may be received at the end of each measurement period, or at some other frequency. In one example, the ultrasound device itself, or some external computing device, may be configured to accept such information as inputs and transmit it to the server or medical professional(s). Further, the ultrasound device and/or the server may be configured to derive correlations between the reported health state of the wearer, and the heart rate measurement(s) transmitted by the ultrasound device. For example, the ultrasound device and/or the server may analyze the heart rate data and the health state data and detect that the wearer has experienced certain adverse health conditions, such as dizziness or a heart attack, when the heart rate reached a certain value. The ultrasound device and/or the server may use this correlation data to generate recommendations for the wearer, or to develop a clinical protocol.

The server that receives the data from the ultrasound device may receive similar data from a plurality of other, similar ultrasound devices. In this way, the server can collect data regarding a plurality of human subjects. This data, including both the physiological parameter measurements and the indications of health state, may, in turn, be used to develop one or more clinical protocols used by the server to generate recommendations and/or used by medical professionals to provide medical care and advice to their patients. This data may further be used to recognize correlations between a physiological parameter and health conditions among the population. Health professionals may further use this data to diagnose and prevent illness and disease, prevent serious clinical events in the population, and to update clinical protocols, courses of treatment, and the standard of care.

Also provided is a method for making an ultrasound device. The method may include forming a coupling material precursor, heating the coupling material precursor, placing the hot coupling material mixture on an ultrasound transducer, and cooling the coupling material mixture to form a coupling material on the ultrasound transducer. The resulting coupling material includes a solid component and a liquid component, wherein the liquid component is absorbed within the solid component and forms a microscopic liquid layer on a surface of the solid component.

The present disclosure also provides a method for using an ultrasound device. The method may include (i) contacting a target surface with an ultrasound device having a coupling layer as described above, and (ii) transmitting an acoustic signal from the ultrasound transducer to the target surface via the coupling layer.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. EXAMPLE COUPLING MATERIAL

Coupling materials are typically used with ultrasound transducers to minimize acoustic impedance mismatches as sound waves travel from the transducer into the target surface and back. Because there is a large acoustic mismatch between gases and solids or liquids, any gas (e.g., air) present between the transducer and the target surface will have a negative effect on the ultrasound results.

Coupling materials reduce acoustic impedance mismatches by reducing the amount of air between the transducer into the target surface. Coupling materials used with ultrasound devices are typically water based liquid gels that are applied to the target surface (e.g., human skin) and/or the ultrasound transducer. However, the use of wet coupling gels is not practical in a long-term device, especially in the case of a wearable consumer device. Dry solid coupling materials are also not optimal because that don't fully remove the air interface and are therefore less efficient couplers.

Figure 1:
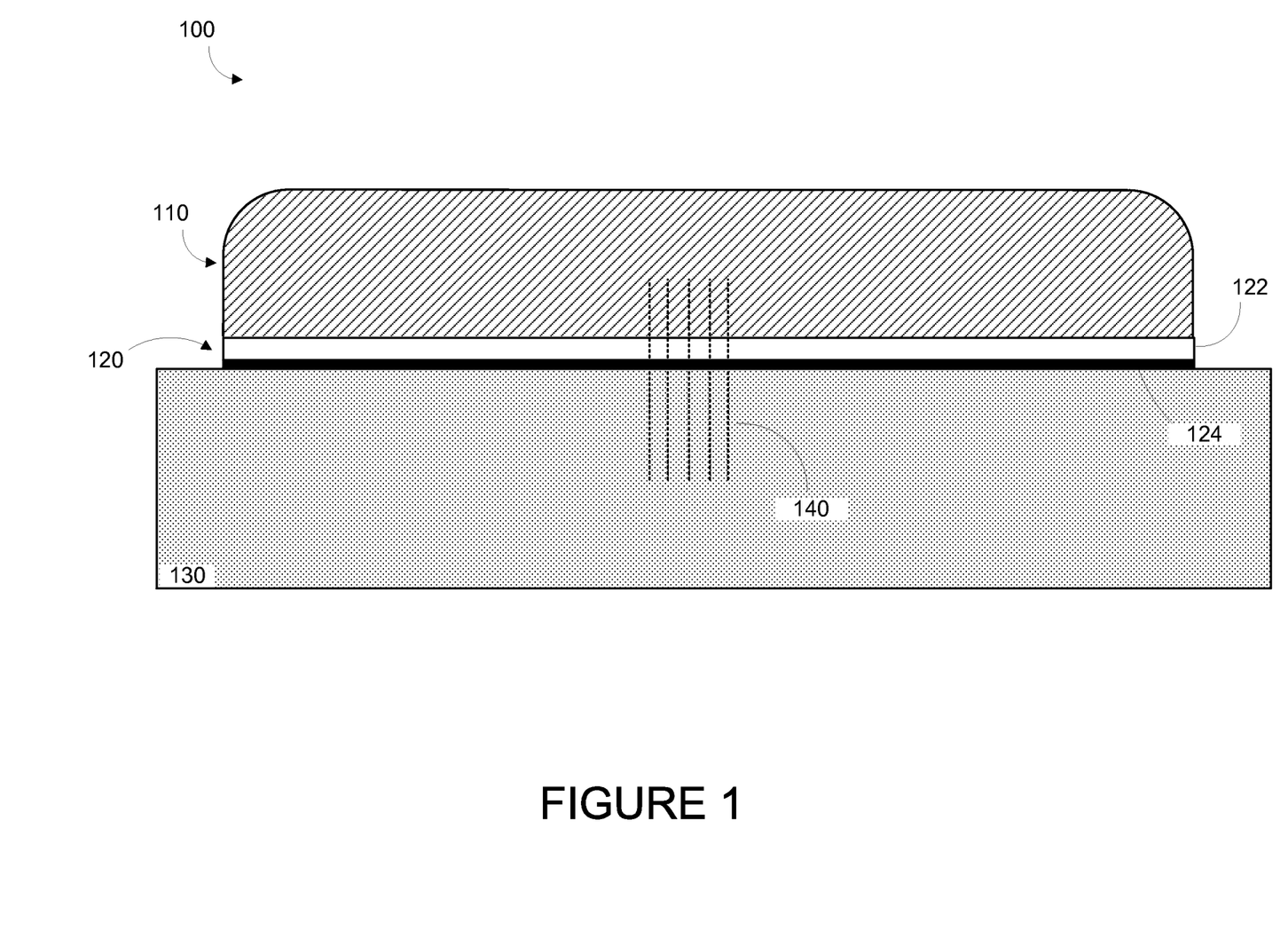
FIG. 1 is a perspective view of an example of an ultrasound device.

FIG. 1 provides a cross-section view of an ultrasound device 100, which includes an ultrasound transducer 110 and a coupling material 120. The coupling material includes a macroscopic solid component 122 and a microscopic liquid layer 124. The solid component 122 is in contact with the ultrasound transducer 110, and the liquid layer 124 is on the surface of the solid component 122. When the ultrasound device 100 is contacted with a target surface 130, the liquid layer 124 is capable of filling substantially all of the gaps and spaces between the ultrasound transducer 110 and the target surface 130. The coupling material 120 is capable of conducting acoustic energy 140 from the ultrasound transducer 110 to the target surface 130 via the liquid layer 124. In some embodiments, the coupling material has a Shore 00 hardness between about 1 and about 50. In other embodiments, the Shore 00 hardness of the coupling material is between about 1 and about 10, about 10 and about 20, about 20 and about 30, about 30 and about 40, about 40 and about 50, about 10 and about 30, or about 20 and about 40.

The coupling material of the ultrasound device may have a solid component and a liquid component. The liquid component can be sufficiently absorbed within the solid component so that the liquid component forms a microscopic liquid layer on a surface of the solid component. Ideally, a solid material is chosen that can absorb and bind the liquid material in large amounts, i.e. the weight of the absorbed liquid is many times the weight of the solid itself. The result is a solid coupling material that maintains a microscopic layer of surface liquid. This allows the solid coupling material to reduce the amount of air between the ultrasound transducer and the target surface, thus reducing acoustic impedance mismatches while not drying out.

The solid component can be saturated with the liquid component. The liquid and solid components can have a high chemical and/or physical affinity for each other. For example, the solid and liquid components may chemically (e.g., covalent or ionic bonding) or physically bind (e.g., non-bonding interactions such as electrostatic interactions, dipole interactions, van der Waals forces, hydrogen bonding, dispersion forces, etc.). As a result, the liquid does not separate from the solid at a macroscopic level when squeezed (as a sponge would). In some embodiments, the ultrasound device may leave a residue on the target surface. For example, upon removal of the ultrasound device from the skin surface, the coupling material may leave a residual layer no thicker than 100 μm.

The surface of the coupling material can include a microscopic layer of liquid. The liquid layer can be about 1-50 μm in thickness. In some embodiments, the liquid layer is present under ambient conditions. When the coupling material is compressed, it may maintain substantially the same thickness of microscopic liquid layer. In other embodiments, compression may increase the thickness of the liquid layer. The liquid layer may also present upon subjecting the coupling material to non-ambient conditions. For example, the liquid layer may present at increased or decreased temperature, electrical charge, change in pressure, sonication, etc.

In some examples, the solid component is the minor component of the coupling material (i.e., less than 50% of the coupling material by weight). For example, the solid component can be about 1% to about 20%, about 5% to about 25%, about 10% to about 30%, about 15% to about 35%, about 20% to about 40% or about 25% to about 45%. In some embodiments, the solid component can be about 1% to about 5%, about 5% to about 10%, about 10% to about 15%, about 15% to about 20%, about 20% to about 25%, about 25% to about 30%, about 35% to about 40%, or about 40% to about 45% of the coupling material by weight. In other embodiments, the solid component can be about 1% to about 10%, about 5% to about 15%, about 10% to about 20%, about 15% to about 25%, about 20% to about 30%, about 25% to about 35%, about 30% to about 40%, or about 35% to about 45% of the coupling material by weight.

In some embodiments, the coupling material can be non-aqueous. The solid component of the coupling material can be non-water soluble, and can include molecules having long chains, such as a long-chain polymer. The polymer of the solid component can be a hydrocarbon polymer, silicone polymer or fluorosilicone polymer, or mixture thereof. The liquid component of the coupling material can also be non-aqueous, such as a low vapor pressure liquid (e.g., an oil). The oil of the liquid component can include a hydrocarbon oil, silicon oil or fluorosilicone oil, or mixture thereof.

The properties of the non-aqueous coupling material can be adjusted by altering the type of solid and liquid components. In some embodiments, the non-aqueous coupling material includes a solid component comprising a hydrocarbon polymer, and a liquid component comprising a hydrocarbon oil. In some embodiments, the non-aqueous coupling material includes a solid component comprising a silicone polymer, and a liquid component comprising a silicone oil. In other embodiments, the non-aqueous coupling material includes a solid component comprising a fluorosilicone polymer, and a liquid component comprising a fluorosilicone oil. In some examples, the non-aqueous coupling material includes a mixture of components, where one or more solid components are selected from hydrocarbon polymer, silicon polymer and fluorosilicone polymer, and one or more solid components are selected from hydrocarbon oil, silicon oil and fluorosilicone oil.

The properties of the non-aqueous coupling material can also be adjusted by altering the ratio of solid component to liquid component. In some examples, the solid component is the minor component of the coupling material (i.e., less than 50% of the coupling material by weight). For example, the solid component can be about 1% to about 20%, about 5% to about 25%, about 10% to about 30%, about 15% to about 35%, about 20% to about 40% or about 25% to about 45%. In some embodiments, the solid component can be about 1% to about 5%, about 5% to about 10%, about 10% to about 15%, about 15% to about 20%, about 20% to about 25%, about 25% to about 30%, about 35% to about 40%, or about 40% to about 45% of the coupling material by weight. In other embodiments, the solid component can be about 1% to about 10%, about 5% to about 15%, about 10% to about 20%, about 15% to about 25%, about 20% to about 30%, about 25% to about 35%, about 30% to about 40%, or about 35% to about 45% of the coupling material by weight.

In some examples, the non-aqueous coupling material can include paraffin and mineral oil. The paraffin can be a mixture of hydrocarbon molecules containing between twenty and forty carbon atoms. The paraffin can be solid at room temperature (i.e., around 25° C.), but may begin to melt above 50° C. The mineral oil can include paraffinic oils (n-alkane based), naphthenic oils (cycloalkane based) or aromatic oils (aromatic hydrocarbon based), or mixtures thereof. The mineral oil may be a liquid by-product of petroleum distillation.

The ratio of paraffin to mineral oil can range from about 1:1 to about 5:95. In some embodiments, the coupling material can include a commercially available material, such as Penreco-CP9000, and mineral oil. In such embodiments, the ratio of mineral oil to Penreco-CP9000 can range from about 1:1 to about 10:1. In some embodiments, the ratio of Penreco-CP9000 to mineral oil is about 5:1.

In other embodiments, the non-aqueous coupling material can include a silicone polymer and silicone oil. For example, the coupling material can include dodecamethylpentasiloxane oil and Sylgard 184 silicone. Other silicone polymers and oils that are suitable for the non-aqueous coupling material include polydimethylsiloxanes and polyphenylmethyl siloxanes.

In other embodiments, the non-aqueous coupling material can include a fluorosilicone polymer and fluorosilicone oil. For example, the coupling material can include a suitable silicone polymer or oil described herein where at least one of the substituents on a silicon atom is replaced with a fluorine atom or a group containing fluorine. For example, the fluorosilicone oil could be a polydimethylsiloxane oil where at least one of the methyl groups is replaced with trifluoromethyl.

The fluorosilane coupling materials may be formed by the polymerization of precursor flourosilicone monomers in the presence of a fluorosilicone oil. In such embodiments, the characteristics of the coupling material can be controlled by adjusting the parameters of the polymerization, such as ration of the precursor components, polymerization temperature, and the type and percentage of polymerization catalyst.

In other embodiments, the coupling material can be aqueous. The aqueous coupling material can include a water liquid component and a solid component that includes a polymer network and a super-hygroscopic agent. The polymer network can include cross-linked polymers, for example, a hydrogel polymer. The super-hygroscopic agent can include any material capable of absorbing more than its own weight in water. For example, the super-hygroscopic agent can include silica or polyacrylate. In embodiments where the coupling material is aqueous, the coupling material may further include a biocide to limit fungal or bacterial contamination. Furthermore, in embodiments where the coupling material is aqueous, it may be provided in a dry state, with atmospheric moisture and/or perspiration of the wearer supplying a constantly replenished aqueous component. This is what prevents the coupling material from drying out.

III. EXAMPLE WEARABLE ULTRASOUND DEVICE

An ultrasound device can be used to measure physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the skin or tissue (i.e., target surface) where a lumen is easily observable by ultrasound. A mount, such as a belt, wristband, ankle band, etc. can be provided to mount the device on the body surface. The mount may prevent the wearable device from moving relative to the body to reduce measurement error and noise. In one example, the mount may take the form of a strap or band that can be worn around a part of the body. Further, the mount may be an adhesive substrate for adhering the wearable device to the body of a wearer.

Figure 2A:
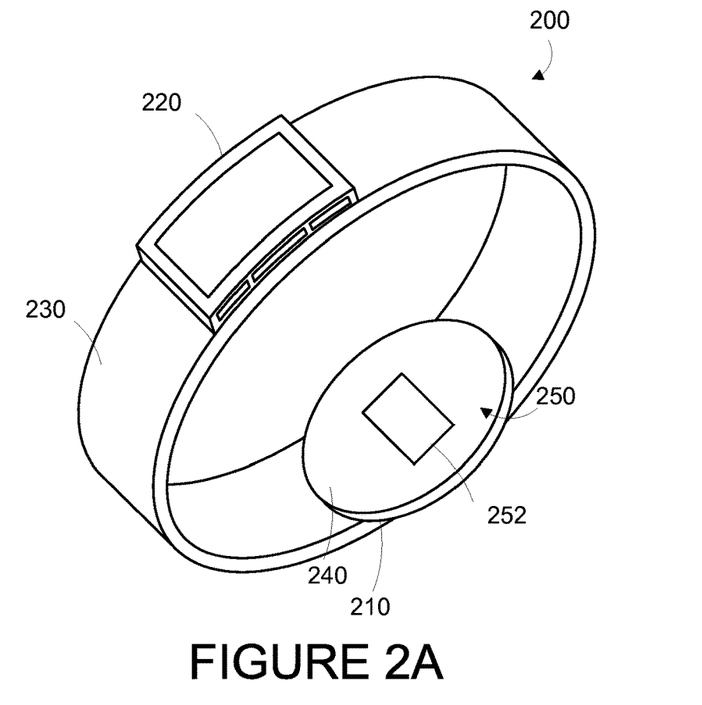
FIGS. 2A and 2B are perspective views of example wearable ultrasound devices.
Figure 2B:
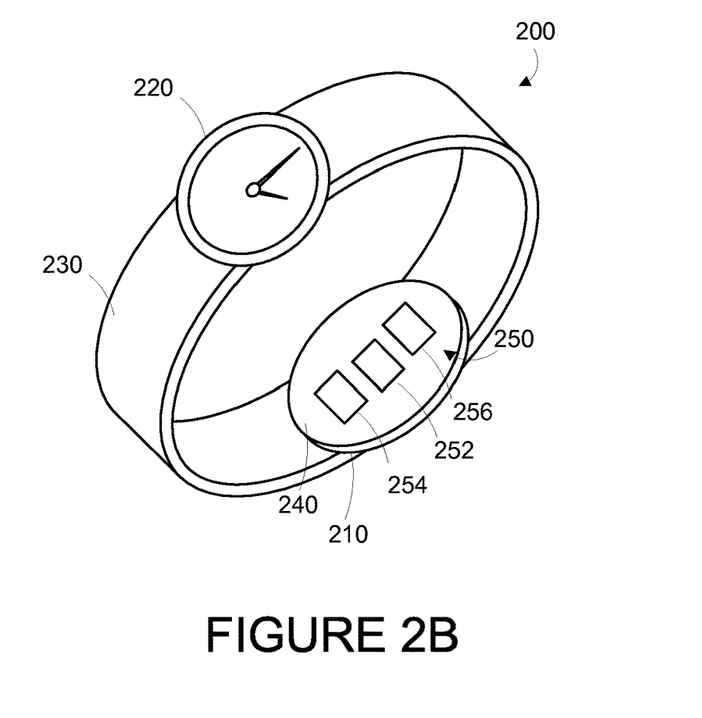

In some examples, as shown in FIGS. 2A and 2B, the measurement platform 210 and user interface 220 of the wrist-mounted device 200 may be provided on different sides of the wearer's arm. In some examples, the user interface 220 is integrated with a watch face or equivalent electronics disposed on the strap 230. While an analog watch is depicted in FIG. 2B, one of ordinary skill in the art will recognize that any type of clock may be provided, such as a digital clock.

As can be seen in FIGS. 2A and 2B, the inner face 240 of the measurement platform 210 is intended to be worn proximate to the wearer's body. A data collection system 250 housed on the measurement platform 210 may include an ultrasound transducer 252 alone (as in FIG. 2A), or include additional detectors 254 and 256 (as in FIG. 2B).

Figure 3A:
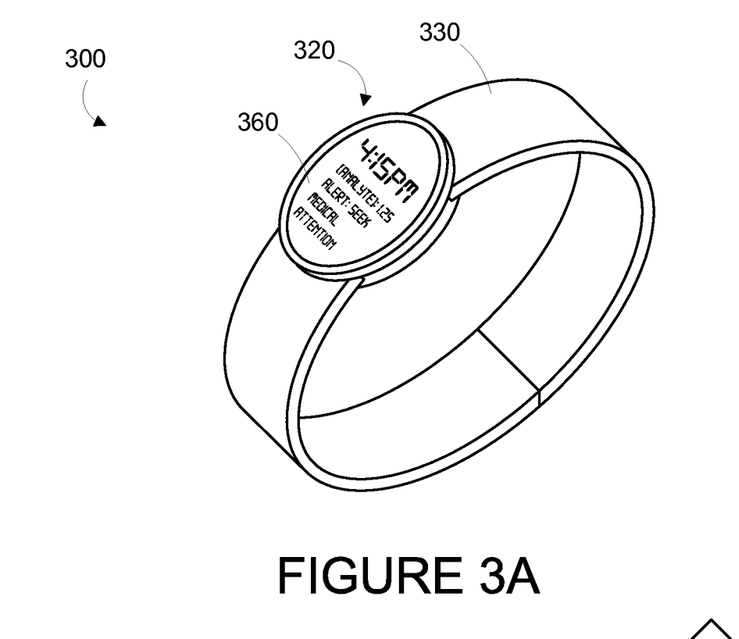
FIGS. 3A and 3B are perspective views of example wearable ultrasound devices.
Figure 3B:
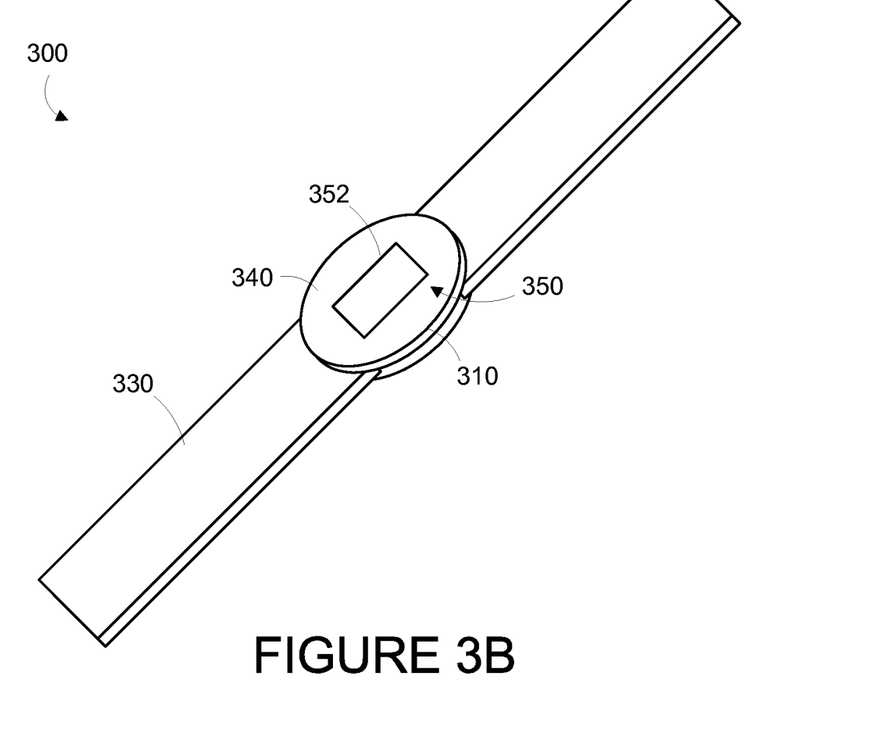

In a further example shown in FIGS. 3A and 3B, a wrist mounted device 300 may have a measurement platform 310 and user interface 320 are provided on the same side of the wearer's arm. Inner face 340 of measurement platform may be positioned proximate to a body surface so that data collection system 350 may interrogate the subsurface vasculature of the wearer's wrist. A user interface 320 with a display 360 may be positioned facing outward from the measurement platform 310. As described above in connection with other embodiments, user interface 320 may be configured to display data collected from the data collection system 350, including physiological parameter(s) and one or more alerts generated by a remote server or other remote computing device, or a processor located on the measurement platform. The user interface 320 may also be configured to display the time of day, date, or other information that may be relevant to the wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. ILLUSTRATIVE METHODS FOR MAKING AN ULTRASOUND DEVICE

The present disclosure also provides methods for making an ultrasound device. The method may include (i) combining a solid component and a liquid component to form a coupling material mixture, (ii) heating the coupling material mixture, (iii) placing the hot coupling material mixture on an ultrasound transducer, and (iv) cooling the coupling material mixture to form a coupling material on the ultrasound transducer, where the coupling material comprises a solid component and a liquid component, where the liquid component is absorbed within the solid component and forms a microscopic liquid layer on a surface of the solid component.

Figure 4:
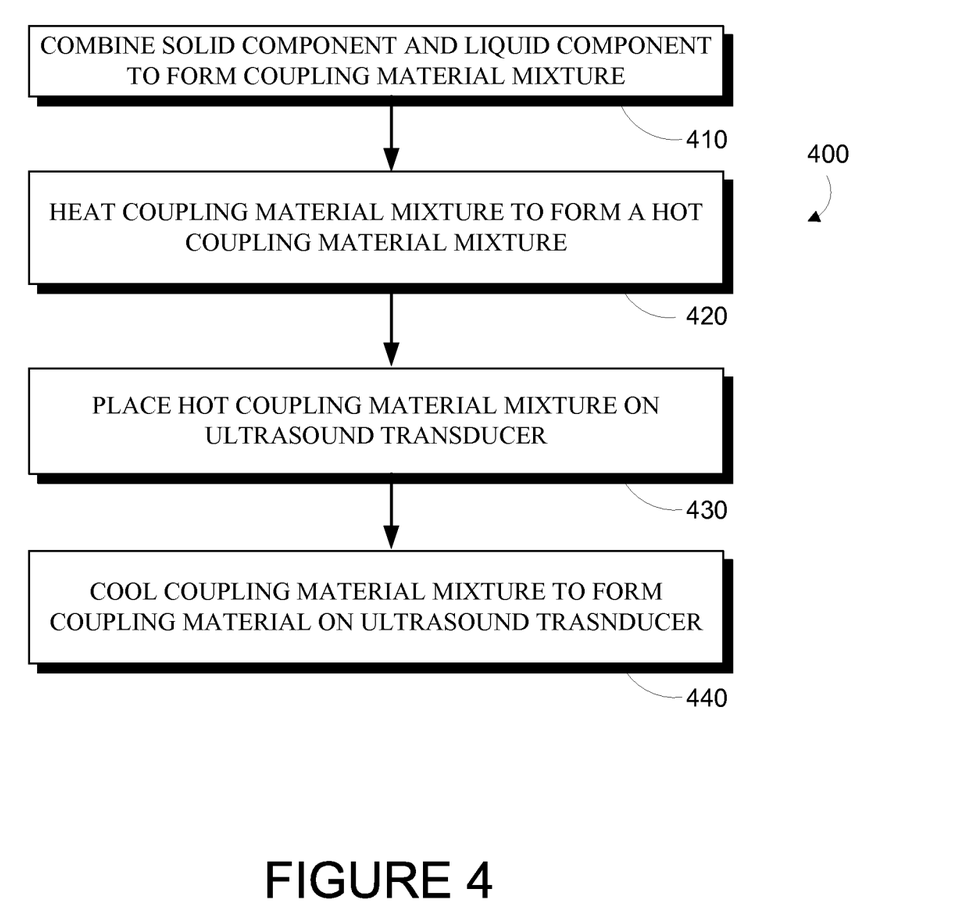
FIG. 4 is a flowchart of an example method for making an ultrasound device.

FIG. 4 is a flowchart of a method 400 for making an ultrasound device. A solid component and liquid component are combined to form a coupling material mixture 410. In some embodiments, the solid component and/or liquid component of the coupling material mixture is a precursor to the solid and/or liquid component of the coupling material of the ultrasound device. The coupling material mixture is heated to form a hot coupling mixture 420. The degree of heating may be dependent on the characteristics of the solid and/or liquid component. In some embodiments, the heating is sufficient to soften the coupling material mixture. In other embodiments, the coupling material mixture is heated to substantially melt the mixture to liquid or gel-like consistency. The hot coupling material mixture is placed on the ultrasound transducer 430. In some embodiments, the hot coupling material mixture substantially covers the surface of the transducer. In other embodiments, the material covers a portion of the transducer. The hot coupling material mixture is cooled to form a coupling material on the ultrasound transducer 440. Cooling may be accomplished by allowing the hot coupling material mixture to cool to ambient temperature (i.e., "air cooled"), or cooling can be accelerated by subjecting the transducer to low temperature or by providing air flow over the material. The resulting cooled coupling material includes a solid component and a liquid component, where the liquid component is absorbed within the solid component and forms a microscopic liquid layer on a surface of the solid component. In alternative embodiments, the liquid component is simply allowed to infuse the solid material in a prolonged immersion process without melting. For example, it is known that silicone rubber can be made to 'swell' to several times its initial volume by immersing it in silicone oil for some time.

V. ILLUSTRATIVE METHODS FOR OPERATING AN ULTRASOUND DEVICE

The present disclosure also provides methods for determining the rate at which a component moves through a portion of lumen. The method may include contacting a target surface with an ultrasound device as described herein, and transmitting an acoustic signal from the ultrasound transducer to the target surface. The acoustic signal of the ultrasound transducer travels to the target surface via the coupling material, which includes a solid component and a liquid component, wherein the liquid component is absorbed within the solid component and forms a microscopic liquid layer on a surface of the solid component, and wherein at least a portion of the microscopic liquid layer contacts the target surface.

In another aspect the disclosure also provides a method for using an ultrasound device. The method may include:
(i) contacting a target surface with an ultrasound device, where the ultrasound device comprises:
    an ultrasound transducer; and
    a coupling material in contact with the ultrasound transducer, where the coupling material comprises a solid component and a liquid component, where the liquid component is absorbed within the solid component and forms a microscopic liquid layer on a surface of the solid component, and where at least a portion of the microscopic liquid layer contacts the target surface; and
(ii) transmitting an acoustic signal from the ultrasound transducer to the target surface via the microscopic liquid layer in contact with the target surface.

In some embodiments, the target surface is an external skin surface of a living body.

Figure 5:
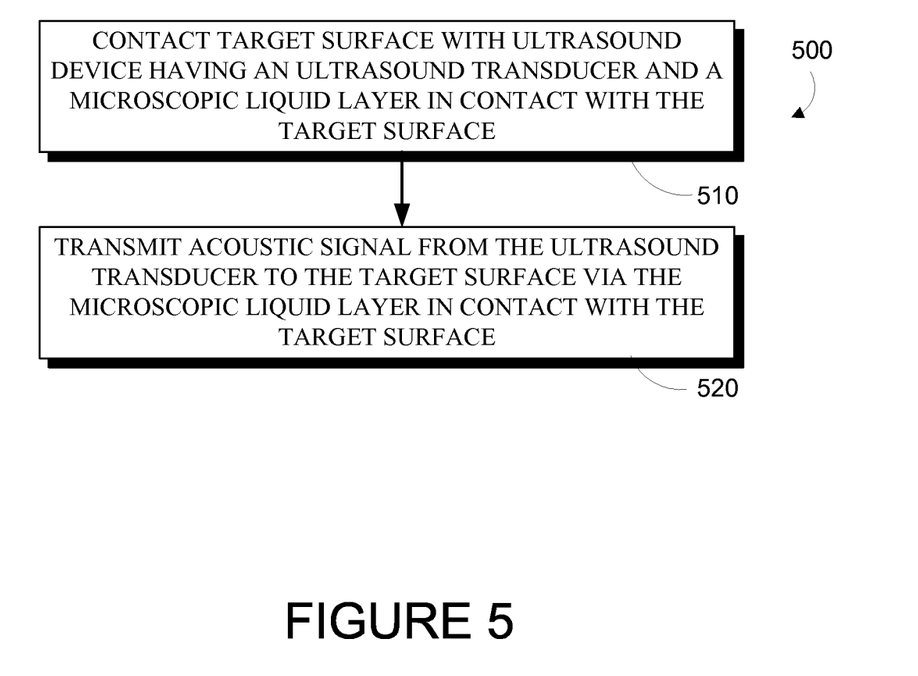
FIG. 5 is a flowchart of an example method for operating an ultrasound device.

FIG. 5 is a flowchart of a method 500 for operating an ultrasound device. The target surface is contacted with an ultrasound device having an ultrasound transducer and a coupling layer, where the coupling layer includes a liquid layer in contact with the target surface 510. An acoustic signal is transmitted from the ultrasound transducer through the microscopic liquid layer into the target surface 520. In some embodiments, the acoustic signal may be a Doppler ultrasound signal.

Some embodiments of the present disclosure also provide a method for monitoring cardiovascular health by detecting the movement of a component through the lumen to determine the flow rate of the component. The method may include a wearable device having a user interface configured to alert the wearer when a monitored physiological parameter is outside a pre-determined acceptable range. The wearable device may also further alert a third party or upload data to a server.

Figure 6:
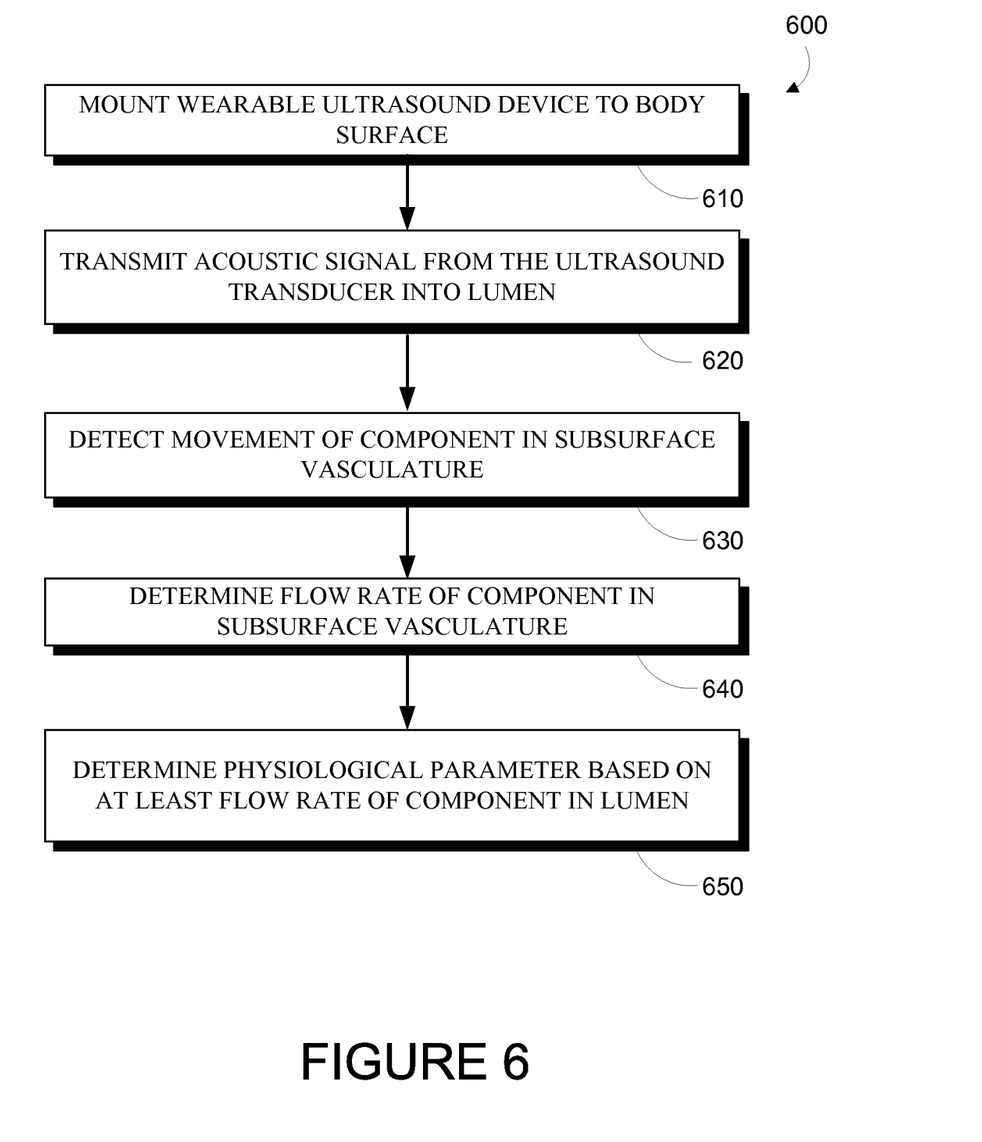
FIG. 6 is a flowchart of an example method for operating an ultrasound device.

FIG. 6 is a flowchart of a method 600 for operating a wearable ultrasound device to take non-invasive, in vivo, real-time measurements of physiological parameters. A wearable device can be mounted to a body surface of a human subject, wherein the body surface is proximate to a portion of subsurface vasculature 610. The wearable ultrasound device, via the ultrasound transducer, transmits an acoustic signal into the portion of the subsurface vasculature 620. The wearable ultrasound device detects the movement of a component present in the subsurface vasculature 630, and determines the flow rate of the component 640. The wearable ultrasound device may then determines a physiological parameter (e.g., heart rate) based at least on the determined flow rate 650.

Figure 7A:
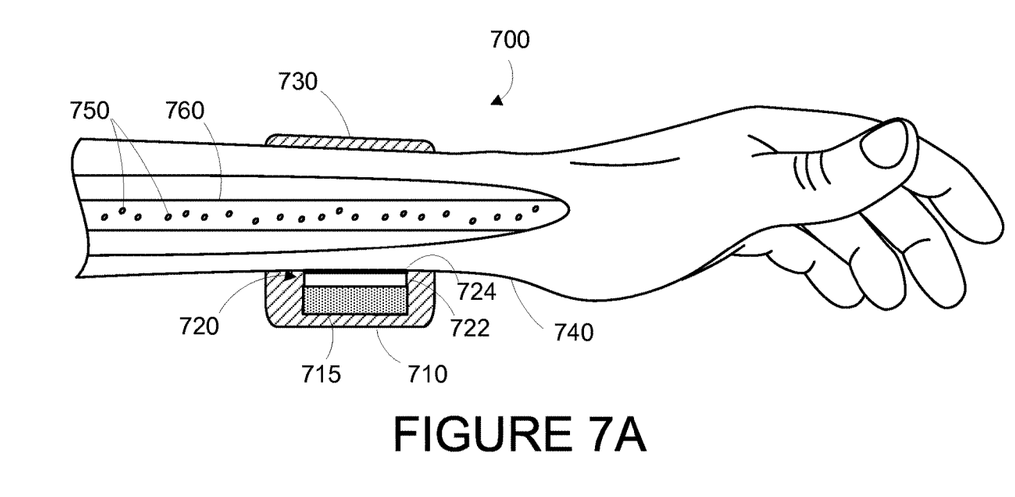
FIG. 7A is a side partial cross-sectional view of a wrist-mounted device, while on a human wrist.
Figure 7B:
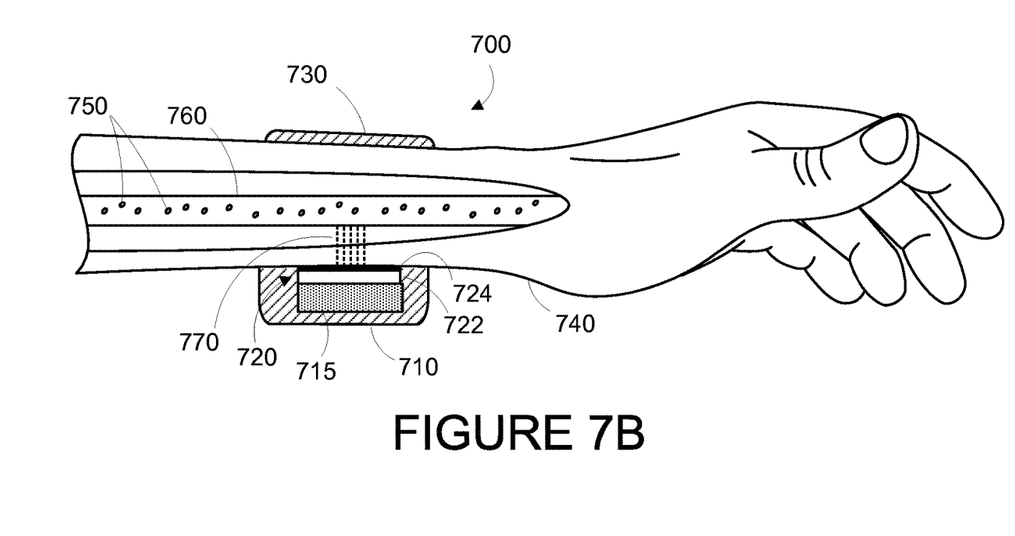
FIG. 7B is a side partial cross-sectional view of a wrist-mounted device, while on a human wrist.

FIGS. 7A and 7B are partial cross-sectional side views of a human wrist illustrating the operation of various examples of a wrist-mounted device. In the example shown in FIGS. 7A and 7B, the wrist-mounted device 700 includes a measurement platform 710 mounted on a strap or wrist-band 730 and oriented on the anterior side 740 of the wearer's wrist. Measurement platform 710 is positioned over a portion of the wrist where components 750 in the subsurface vasculature 760 are easily observable. In this example, measurement platform 710 includes a data collection system having a single ultrasound transducer 715, which has a coupling material 720 between the ultrasound transducer 715 and the anterior side 740 of the wearer's wrist. The coupling material includes a solid component 722 and a liquid component, wherein the liquid component is absorbed within the solid component 722 and forms a microscopic liquid layer 724 on a surface of the solid component 722. FIG. 7A illustrates the state of the subsurface vasculature when measurement device 700 is inactive. FIG. 7B illustrates the state of the subsurface vasculature when measurement device 700 is active. When active, an acoustic signal 770 is transmitted through the coupling material 720 into the portion of subsurface vasculature 760 and the rate at which the components 750 in the subsurface vasculature 760 are traveling is determined.

VI. Conclusion

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:
1. An ultrasound device, comprising:
an ultrasound transducer; and
a coupling material in contact with the ultrasound transducer, wherein the coupling material comprises a solid component and a liquid component, wherein the liquid component is absorbed within the solid component and forms a microscopic liquid layer on an outer surface of the solid component, wherein the microscopic liquid layer is between 1 μm and 50 μm in thickness, wherein the solid component is less than 50% of the coupling material by weight, and
wherein when at least a portion of the microscopic liquid layer contacts a target surface and the ultrasound transducer transmits an acoustic signal, the coupling material conducts acoustic energy from the ultrasound transducer to the target surface via the microscopic liquid layer.
2. The ultrasound device of claim 1, wherein the coupling material has a Shore 00 hardness between about 1 and about 50.
3. The ultrasound device of claim 1, wherein the liquid component is non-aqueous.
4. The ultrasound device of claim 3, wherein the solid component comprises a polymer.
5. The ultrasound device of claim 4, wherein the polymer comprises a hydrocarbon polymer.
6. The ultrasound device of claim 4, wherein the polymer comprises a silicone polymer.
7. The ultrasound device of claim 4, wherein the polymer comprises a fluorosilicone polymer.
8. The ultrasound device of claim 3, wherein the liquid component comprises an oil.
9. The ultrasound device of claim 8, wherein the oil comprises a hydrocarbon oil.
10. The ultrasound device of claim 8, wherein the oil comprises a silicone oil.
11. The ultrasound device of claim 8, wherein the oil comprises a fluorosilicone oil.
12. The ultrasound device of claim 4, wherein
the solid component comprises a hydrocarbon polymer; and
the liquid component comprises mineral oil.
13. The device of claim 12, wherein the solid component is about 1% to about 10% of the coupling material by weight.

14. The ultrasound device of claim 3, wherein
the solid component comprises a silicone polymer; and
the liquid component comprises a silicone oil.

15. The ultrasound device of claim 3, wherein
the solid component comprises a fluorosilicone polymer; and
the liquid component comprises a fluorosilicone oil.

16. The ultrasound device of claim 1, wherein
the liquid component comprises water.

17. The ultrasound device of claim 16, wherein
the solid component comprises a polymer network and a super-hygroscopic agent.

18. The ultrasound device of claim 17, wherein
the polymer network comprises cross-linked polymers.

19. The ultrasound device of claim 17, wherein
the super-hygroscopic agent comprises silica or polyacrylate.

20. The ultrasound device of claim 1, wherein
the target surface is an external skin surface of a living body.

21. The ultrasound device of claim 20, wherein
upon removal of the ultrasound device from the skin surface, the coupling material leaves a residual layer no thicker than 100 μm.

22. A method, comprising:
combining a solid component and a liquid component to form a coupling material mixture;
heating the coupling material mixture;
placing the hot coupling material mixture on an ultrasound transducer; and
cooling the coupling material mixture to form a coupling material on the ultrasound transducer, wherein the coupling material comprises a solid component and a liquid component, wherein the liquid component is absorbed within the solid component and forms a microscopic liquid layer on an outer surface of the solid component, wherein the microscopic liquid layer is between 1 μm and 50 μm in thickness, and wherein the solid component is less than 50% of the coupling material by weight.

23. The method of claim 22, wherein
the solid comprises a polymer; and
the liquid comprises an oil.

24. A method, comprising:
contacting a target surface with an ultrasound device, wherein the ultrasound device comprises:
an ultrasound transducer; and
a coupling material in contact with the ultrasound transducer, wherein the coupling material comprises a solid component and a liquid component, wherein the liquid component is absorbed within the solid component and forms a microscopic liquid layer on an outer surface of the solid component, wherein the microscopic liquid layer is between 1 μm and 50 μm in thickness, wherein the solid component is less than 50% of the coupling material by weight, and wherein at least a portion of the microscopic liquid layer contacts the target surface; and
transmitting an acoustic signal from the ultrasound transducer to the target surface via the microscopic liquid layer in contact with the target surface.

25. The ultrasound device of claim 1, wherein, when the coupling material is squeezed, the microscopic liquid layer does not separate from the solid component at a macroscopic level.

26. The ultrasound device of claim 1, wherein the solid component is non-water soluble.

27. The ultrasound device of claim 1, wherein the ultrasound device is a wrist-mounted device.

* * * * *